(12) United States Patent
Shannon et al.

(10) Patent No.: US 8,162,900 B2
(45) Date of Patent: Apr. 24, 2012

(54) METHOD FOR SUBSTANTIALLY NON-DELAMINABLE SMOOTH VENTRICULAR ASSIST DEVICE CONDUIT AND PRODUCT FROM SAME

(75) Inventors: Donald T. Shannon, Trabuco Canyon, CA (US); Chris Kuo, Anaheim Hills, CA (US); Benny Tu, Lake Forest, CA (US); Mike Randall, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 135 days.

(21) Appl. No.: 12/653,100

(22) Filed: Dec. 7, 2009

(65) Prior Publication Data

US 2010/0094077 A1 Apr. 15, 2010

Related U.S. Application Data

(62) Division of application No. 09/952,462, filed on Sep. 11, 2001, now Pat. No. 7,641,635.

(51) Int. Cl.
*A61M 25/00* (2006.01)
(52) U.S. Cl. ....... 604/192; 623/1.33; 623/1.32; 604/525
(58) Field of Classification Search ........ 623/1.32–1.33; 604/192, 524, 527
See application file for complete search history.

(56) References Cited

U.S. PATENT DOCUMENTS

| 4,336,794 | A | 6/1982 | Chikhama |
| 4,875,468 | A | 10/1989 | Krauter et al. |
| 5,885,209 | A | 3/1999 | Green |
| 6,001,056 | A | 12/1999 | Jassawalla et al. |
| 6,159,565 | A | 12/2000 | Campbell et al. |
| 6,197,014 | B1 * | 3/2001 | Samson et al. ............... 604/524 |
| 6,824,553 | B1 * | 11/2004 | Samson et al. ............... 606/192 |
| 6,960,392 | B2 * | 11/2005 | Le Du et al. ................. 428/461 |
| 7,049,380 | B1 * | 5/2006 | Chang et al. ................. 526/247 |
| 2002/0049489 | A1 * | 4/2002 | Herweck et al. ............ 623/1.13 |
| 2006/0224236 | A1 | 10/2006 | Thistle ....................... 623/1.32 |

FOREIGN PATENT DOCUMENTS

| DE | 27 28 636 | 1/1978 |
| WO | WO 95/22359 | 8/1995 |

* cited by examiner

*Primary Examiner* — Niketa Patel
*Assistant Examiner* — Joseph Stoklosa
(74) *Attorney, Agent, or Firm* — Keith Newburry

(57) ABSTRACT

A method of non-delaminably bonding a non-porous thermoplastic elastomer to a substrate by heating a bilayer of the elastomer and the substrate for a predetermined time and a product obtained by the method. Methods for producing non-delaminable conduits and non-delaminable kink-resistant conduits constructed of biocompatible elastomers and substrates, and products produced by these methods are taught. Methods, products, and articles of manufacture relating to non-delaminable monofilament supported kink-resistive conduits that may be used as inflow conduits in left ventricular assist devices for treatment of heart failure are also provided.

20 Claims, 3 Drawing Sheets

METHOD FOR SUBSTANTIALLY NON-DELAMINABLE SMOOTH VENTRICULAR ASSIST DEVICE CONDUIT AND PRODUCT FROM SAME

CROSS-REFERENCE TO RELATED APPLICATION

This application is a divisional of, and claims priority to, Ser. No. 09/952,462 filed on Sep. 11, 2001 entitled "Method for Substantially Non-Delaminable Smooth Ventricular Assist Device Conduit and Product From Same", now U.S. Pat. No. 7,641,635, which is incorporated herein by reference in its entirety.

BACKGROUND

The present invention is related to methods and apparatus for surgically implantable pumps that provide a mechanical device for augmenting or replacing the blood pumping action of damaged or diseased hearts. More specifically, this invention is related to methods and apparatus for conduits for such pumps to meet the three-fold requirements of a substantially non-delaminable conduit having a highly non-thrombogenic porous inner surface that is not susceptible to air leakage under negative pressure, whereby the use of such implantable pump procedures is broadly enabled, and wherein the functional utility, ease of use, and wide applicability of the device in medical practice constitutes progress in science and the useful arts. Furthermore, the present invention teaches processes to make and use the device in medical practice.

Of all the cardiovascular disorders, congestive heart failure (CHF) is the only one to show a sharp increase in prevalence since the 1960s. This rise in the number of cases of CHF worldwide is a major and growing public health concern. While the prevalence of coronary heart disease (CHD) has declined in the past few decades and the prevalence of stroke has remained steady until recent years, the number of people suffering from CHF has increased dramatically. In terms of mortality and morbidity, the prognosis for CHF is depressingly poor and in the US, the disease has been recognized as 'epidemic'. The high costs associated with the condition will place an added burden on public health resources as the incidence of CHF continues to rise.

By definition, CHF is a disorder in which the heart fails to pump blood adequately to other organs in the body. This can result in a shortness of breath, fatigue and fluid retention (edema) and if left unchecked can lead to death within a few years. CHF is not a disease per se but a condition that arises as a result of various cardiovascular diseases (CVD). In effect, CHF is the end-stage syndrome of heart muscle disorders and diseases such as hypertension and CHD, which can damage or impair the functionality of the heart and the vessels supplying it.

In the majority of cases, CHF is a progressive condition and over time, the ability of the heart muscle to function properly deteriorates—this process is called cardiac remodeling. As the condition worsens, the ventricular muscle over-stretches and the muscle fails to work to its full efficiency. This leads to a further reduction in the cardiac output and exacerbates symptoms of heart failure.

In CHF, the reduced cardiac output causes a fall in arterial pressure leading to the activation of several compensatory reflexes. The sympathetic nervous system is stimulated, resulting in a direct increase in the force of contraction of the heart and a greater venous return as a response to venoconstriction. Long-term compensation includes the activation of the renin angiotensin system (RAS) and subsequent renal fluid retention. The combined effect of these responses can lead to the formation of edema, especially in the legs and ankles. If heart failure occurs in the left side of the heart, pulmonary edema can result which manifests as breathlessness. In advanced CHF, the severity of the symptoms can be disabling and often leads to hospitalization. An added consideration is sudden cardiac death, which can occur at any time during the course of CHF.

The most common classification of CHF is based on criteria set out by the New York Heart Association (NYHA). Originally published in 1928, the classifications defined the stages of CHF by its clinical severity and the functional status of the cardiac muscle. Over the years the classifications have been updated and the latest revision was in 1994. The NYHA classes of CHF are listed below.

New York Heart Association Functional Classifications of CHF

Class I Patients with cardiac disease but no resulting limitation of physical activity. No fatigue, palpitations, shortness of breath or angina during normal physical activity.

Class II Patients with cardiac disease with slight limitation of physical activity. Normal physical activity results in symptoms of heart failure or angina but the patient is comfortable at rest.

Class III Patients with cardiac disease with marked limitation of physical activity. Slight physical activity results in fatigue, palpitations, shortness of breath or angina but comfortable at rest.

Class IV Patients with cardiac disease and an inability to carry out physical activity without discomfort. Even at rest, the symptoms of heart failure or angina may be present.

The failing heart is a result of a number of factors combining to reduce the efficiency of the heart as a pump. The most common dysfunction is an impairment of left ventricular function, which is present in 80-90% of patients with CHF. As the blood flow from the heart slows, the blood returning to the heart through the veins can back-up, resulting in congestion in the tissues. This can lead to swelling in the legs and ankle and fluid retention in the lungs, which interferes with breathing and contributes to the characteristic shortness of breath seen in people with CHF.

Several types of surgically implantable pumps have been developed in an effort to provide a mechanical device for augmenting or replacing the blood pumping action of damaged or diseased hearts. Some of these pumps are designed to support single ventricular function. Such pumps usually support the left ventricle, which pumps blood to the entire body except the lungs, since it becomes diseased far more commonly than the right ventricle, which pumps blood only to the lungs. Other devices have been tested and used for providing biventricular function.

Depending on the needs of a particular patient and the design of a pump, pumping units such as so-called "VADs" (ventricular assist devices) can be implanted to assist a functioning heart that does not have adequate pumping capability. Left-ventricular assist devices (LVAD) in particular are recognized as potentially very valuable for assisting patients who suffer from congestive heart failure. An LVAD is able to fully take over the function of the left ventricle, thus perfusing the body with oxygen-rich blood.

The LVAD attaches to the patient's natural heart, and to a natural artery, and can be removed if the natural heart recovers. Some LVADs are surgically implanted into the patient's abdominal cavity, while others remain outside the body and are placed in fluid communication with the heart via elongated cannulas. Recently, a National Institutes of Health study estimated that as many as thirty-five thousand people could be candidates for use of a left-ventricular assist device.

At present, conventional ventricular assist devices are used for patients who are waiting for a heart transplant (a so-called, "bridge to transplant"), or alternatively to patients whose natural heart is of such poor condition that the patient cannot be removed from a heart-lung machine without providing some assistance to the patient's heart following otherwise successful open-heart surgery. Still another group of patients eligible for the use of conventional ventricular assist devices are those who suffer massive heart attacks that lead to circulatory collapse. The suitability of long-term utilization of conventional left-ventricular assist devices outside of the clinical environment remains under study.

Expansion and contraction of a variable-volume chamber typically effect blood flow in the LVAD. One-way valves associated with the inflow and outflow ports of the LVAD permit blood flow propelled by the natural left ventricle into the variable-volume chamber during expansion, and blood flow out of this chamber, usually to the ascending thoracic aorta. These one-way flow valves may be constructed as part of the LVAD itself, or may be disposed in separate blood-flow conduits attached thereto. A pair of artificial blood conduits respectively connect the inlet port of the variable-volume chamber (or the inlet end of a valved conduit) to the left ventricle and the outlet port of the variable-volume chamber (or the outlet end of a second valved conduit) to the major artery which is to receive the blood flow from the device.

As is well known, artificial blood conduits have become a valuable tool of modern medicine. One use of such artificial blood conduits is as a temporary or permanent prosthetic artery. Another use is in the connection of temporary blood pumps, such as ventricular assist devices described herein, between the left ventricle of the heart and a major artery.

The demands on artificial blood conduits in ventricular assist devices are great. The conduit must deal with the pulsatile blood flow created by the host's own heart, as well as with the flow, pressure, and pulsations created by the assist device. Moreover, there are differences in flow and pressure between the inflow and outflow conduits connected to the pumping device. For example, while the outflow conduit experiences regular pulses of high pressure, flow in the inflow conduit is dependent on the pumping strength and rhythm of the natural left ventricle on top of which the periodic LVAD pressures are superimposed (i.e., expansion of the variable volume chamber tends to pull fluid from the inflow conduit). The inflow conduit thus sees irregular and typically low flows and pressures; here, the negative pressure transients that can occur in the inflow conduit are of special importance.

Conventional artificial conduits for use in LVADs may be constructed of an elongate flexible woven polyethylene terephthalate (PET) fabric tube. In some cases, the conduits are sealed with a thin bio-compatible collagen coating on the inner lumen wall to render the fabric more leak resistant at the time of implantation, and also more compatible with the patient's blood. The collagen coating, typically bovine collagen, eventually is absorbed into the blood stream and is replaced with a natural coating of blood cells, serum protein, and other elements from the blood. In the absence of a sealant, the conduit may have to be pre-clotted by the surgeon just prior to implantation.

As is generally known in the art, a porous surface on the inner lumen wall of an implanted blood conduit is advantageous because it becomes coated with the natural coating of blood cells, serum protein, and other elements from the blood. This coating inhibits clot formation (thrombogenesis) which is highly desirable. Earlier inflow conduits comprised PET woven grafts surrounded by a machined flexible housing. However, such conduits alternately collapsed and regained their tubular shape with each stroke of the pump. Prior art improvements comprised creating a scaffolding which prevented the collapse of the conduit with each pump stroke. however, since the tube no longer collapsed, the lumen of the tube experienced negative pressure and atmospheric air consequently infiltrated through the walls into the lumen.

Porosity also renders an inflow conduit vulnerable to the entrance of air during the intervals of negative pressure transients that can occur in the inflow conduit as noted above. This raises a serious problem whenever the inflow conduit is in contact with the atmosphere. For example, the surgical implantation of the device entails operation of the LVAD or VAD during the period when the chest of the patient is open to the atmosphere. Likewise, externally mounted LVAD's may have inflow conduits in contact with the atmosphere. Air can be sucked into the inflow conduit during intervals of negative pressure transients as outlined above, leading to air embolisms in the cardiovascular system of the patient undergoing the implantation procedure. Such air embolisms can lead to injury to the patient or even to the death of the patient. It is obvious, therefore, that this risk of air embolisms resulting from the vulnerability of the inflow conduit to the entrance of air during intervals of negative pressure, whenever the inflow conduit is in contact with the air, is an extremely serious problem. Even if the conduits are sealed with a thin bio-compatible collagen coating on the inner lumen wall to render the fabric more leak resistant at the time of implantation this procedure only addresses the problem of leakage of the lumen contents outward, and does not at all address the problem of the entrance of air during the intervals of negative pressure transients that can occur in the inflow conduit as noted above.

Some non-implantable ventricular assist devices utilize cannula-like conduits that are relatively rigid, some being formed of smooth, reinforced non-porous polyurethane. Such conduits might solve the problem of leakage into the conduit lumen when it is under negative pressure, but they would not be suitable for use in implantable devices, as they will not easily accommodate varying anatomical placements, and tend to kink if bent.

My prior invention of an implantable ventricular assist device disclosed in U.S. Pat. No. 6,001,056, which is expressly incorporated herein in its entirety by reference, comprises an inflow conduit. The inflow conduit includes a flexible tubular graft body having an upstream end and a downstream end, the body having a substantially smooth inner surface for enhanced flow-through of blood with a minimum of surface-induced turbulence. The inflow conduit also includes a ventricular attachment structure to which the upstream end of the body connects, and a coupling fitting on the downstream end of the body. An implantable pumping portion may be placed in flow communication with the inflow conduit and with an outflow conduit. The tubular graft body may be a knitted fabric having a biocompatible sealant impregnated therein, or a closed structured PTFE.

Even in the case of an inflow conduit fabricated from closed structured PTFE in which the tubular wall of the conduit has a pore size of not less than 2.mu., the water entry pressure for the base tube is still at least about 5 psi. Even when a thin PTFE tape having a thickness of about 0.01 mm and an ethanol bubble point of at least about 2 psi is wrapped about and laminated to the base tube the resulting extremely low porosity tubular wall still leaks air into the lumen of the tube when placed under negative pressure. Thus, even this device does not solve the twin requirements of a conduit having a highly non-thrombogenic porous inner surface that is not susceptible to leakage under negative pressure.

My prior invention of a non-porous smooth ventricular assist device conduit solves this problem. It is disclosed in copending U.S. patent application Ser. No. 09/874,846 filed Jun. 5, 2001, which is expressly incorporated herein in its entirety by reference, is directed to an improved inflow conduit for an implantable ventricular assist device having a flexible, porous tubular graft body that has an upstream end and a downstream end. The tubular graft body has a substantially smooth inner surface for enhanced flow-through of blood with a minimum of surface-induced turbulence, a ventricular attachment structure to which the upstream end of the body connects, and a coupling fitting on the downstream end of the body. The improvement comprises covering the flexible porous tubular graft body with an attached non-porous polymer, whereby a nonporous conduit is formed. The attached non-porous polymer may be attached by thermal bonding, or by a biocompatible adhesive.

Although this latter conduit uniquely solves the problem of air leakage, the possibility of delamination of the attached non-porous polymer of the conduit of the invention could once again permit such leakage. In view of the absence of methods and apparatus for conduits that meet the three-fold requirements of a substantially non-delaminable conduit having a highly non-thrombogenic porous inner surface that is not susceptible to air leakage under negative pressure, there remains a need for a substantially non-delaminable smooth ventricular assist device conduit and process for making same.

Thus, in spite of extended efforts in academic medicine and the pharmaceutical industry, there remains room for improvement in the construction and function of conduits for ventricular assist devices. Even though conduits for LVAD's are used extensively in medical practice, prior devices, products, or methods available to medical practitioners have not adequately addressed the need for non-delaminable apparatus for conduits for LVAD's to meet the need for methods and apparatus for conduits for such pumps as outlined above. The present invention embraces and finally addresses the clear need for advanced non-delaminable apparatus for conduits for LVAD's and VAD's to meet the three-fold requirements of a substantially non-delaminable conduit having a highly non-thrombogenic porous inner surface that is not susceptible to air leakage under negative pressure as set forth above. Thus, as pioneers and innovators attempt to make methods and apparatus for LVAD's safer, cheaper, more universally used, and of higher quality, none has approached same in combination with simplicity and reliability of operation, until the teachings of the present invention. It is respectfully submitted that other references merely define the state of the art or show the type of systems that have been used to alternately address those issues ameliorated by the teachings of the present invention. Accordingly, further discussions of these references has been omitted at this time due to the fact that they are readily distinguishable from the instant teachings to one of skill in the art.

OBJECTS AND SUMMARY OF THE INVENTION

Accordingly, it is an object of the present invention to provide a method of substantially non-delaminably bonding a substantially non-porous thermoplastic elastomer to a substrate. A further object of the present invention is to provide a substantially non-delaminable conduit for LVAD's that has a highly non-thrombogenic porous inner surface and is not susceptible to air leakage under negative pressure. Another object of the present invention to provide a substantially non-delaminable conduit for LVAD's that has a highly non-thrombogenic porous inner surface, is not susceptible to air leakage under negative pressure, and is relatively safe for the patient. Still another object of the present invention is to provide a substantially non-delaminable conduit for LVAD's, wherein said conduit has a highly non-thrombogenic porous inner surface, is not susceptible to air leakage under negative pressure, and is relatively easy to use. An additional object of the present invention is to provide a substantially non-delaminable conduit for LVAD's that is comparatively cost-effective to manufacture. Even still a further object of the present invention is to provide a substantially non-delaminable conduit for LVAD's that has a highly non-thrombogenic porous inner surface, is not susceptible to air leakage under negative pressure, and is supported by a substantially non-delaminable support structure. Yet still a further object of this invention is to provide methods and apparatus that are suitable for use with the variety of polymeric materials that are used in LVAD devices. Even still another object of this invention is to provide a LVAD apparatus that allows the surgical practitioner to operate the apparatus in the open chest of the patient during the implantation procedure. Even yet still another object of this invention is to provide a method for the treatment of congestive heart failure using a LVAD apparatus that allows the surgical practitioner to operate the apparatus in the open chest of the patient during the implantation procedure. Even an additional object of this invention is to provide an article of manufacture for packaging the apparatus of the invention.

These and other objects are accomplished by the parts, constructions, arrangements, combinations and subcombinations comprising the present invention, the nature of which is set forth in the following general statement, and preferred embodiments of which—illustrative of the best modes in which applicant has contemplated applying the principles—are set forth in the following description and illustrated in the accompanying drawings, and are particularly and distinctly pointed out and set forth in the appended claims forming a part hereof.

BRIEF EXPLANATION OF THE DRAWINGS

The foregoing and other objects and advantages of the invention will be appreciated more fully from the following further description thereof, with reference to the accompanying drawings in which like parts are given like reference numerals and wherein.

DETAILED DESCRIPTION OF THE PREFERRED EMBODIMENTS

Figure 1:
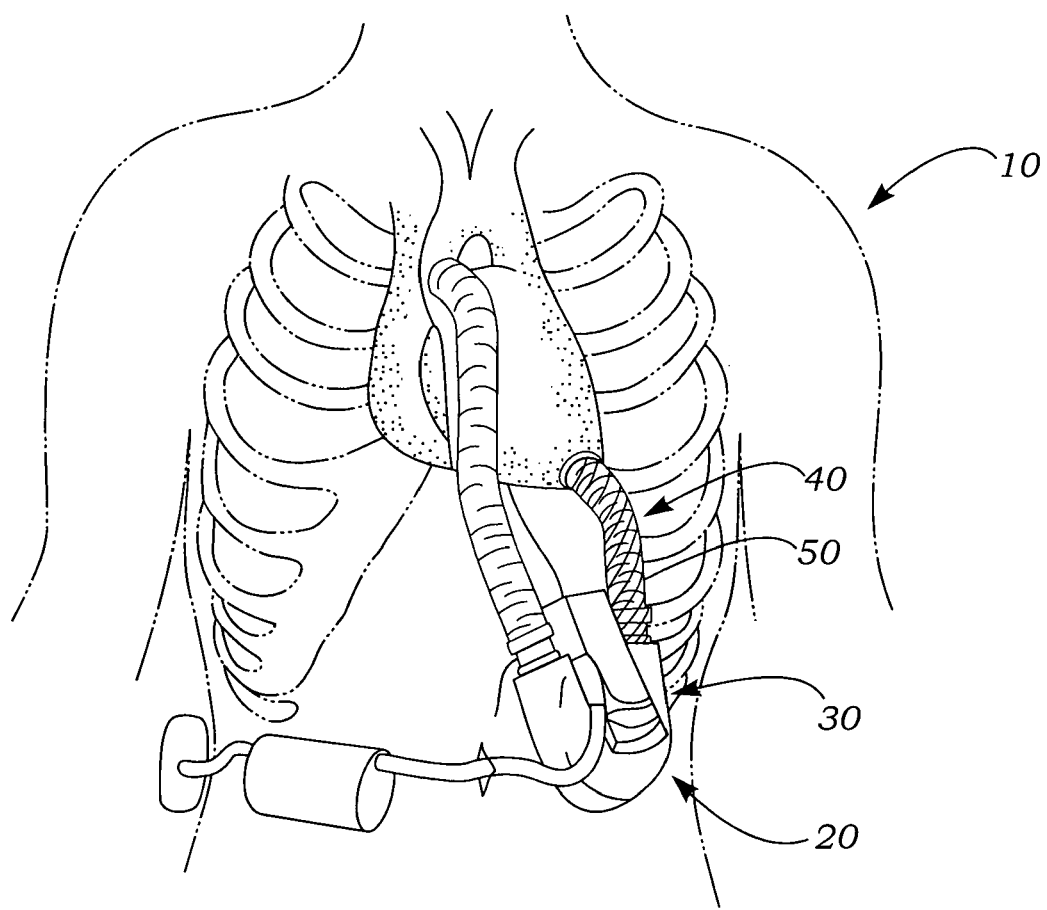
FIG. 1 is a front view of a left ventricular assist system incorporating the present invention connected to the heart of a patient (shown in phantom)
Figure 2:
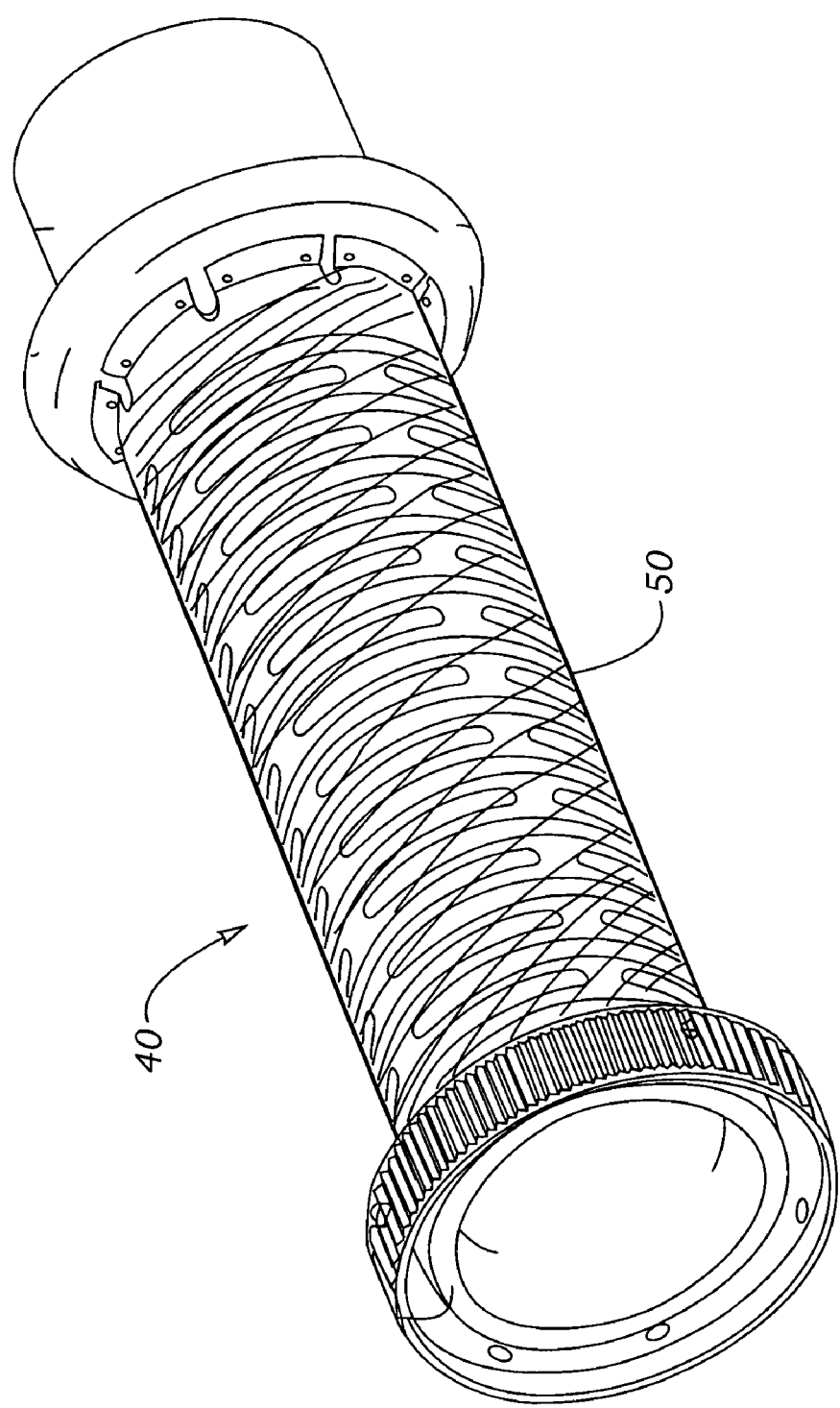
FIG. 2 is a perspective view of an inflow conduit of the present invention; and, FIG. 3 is a perspective view of a further embodiment of an inflow conduit of the present invention.

With reference to FIGS. 1 and 2, a living human host patient 10 with an open chest is shown in fragmentary front elevational view, and with parts of the patient's anatomy shown in phantom or removed solely for better illustration of the salient features of the present invention. Surgically implanted into the patient is the pumping portion 20 of a ventricular assist device, generally referenced with the numeral 30. Ventricular assist device 30 includes an inflow conduit 40 which further includes a substantially non-porous conduit 50 for communicating blood from the patient's left ventricle into the pumping portion 20. As shown in FIG. 2, conduit 50 comprises a flexible, porous tubular substrate to which a substantially non-porous thermoplastic elastomer is substantially non-delaminably bonded in accordance with a method of the invention. An end of inflow conduit 40 is connected to the patient's heart by sutures so that blood flow communication is established and maintained.

Figure 3:
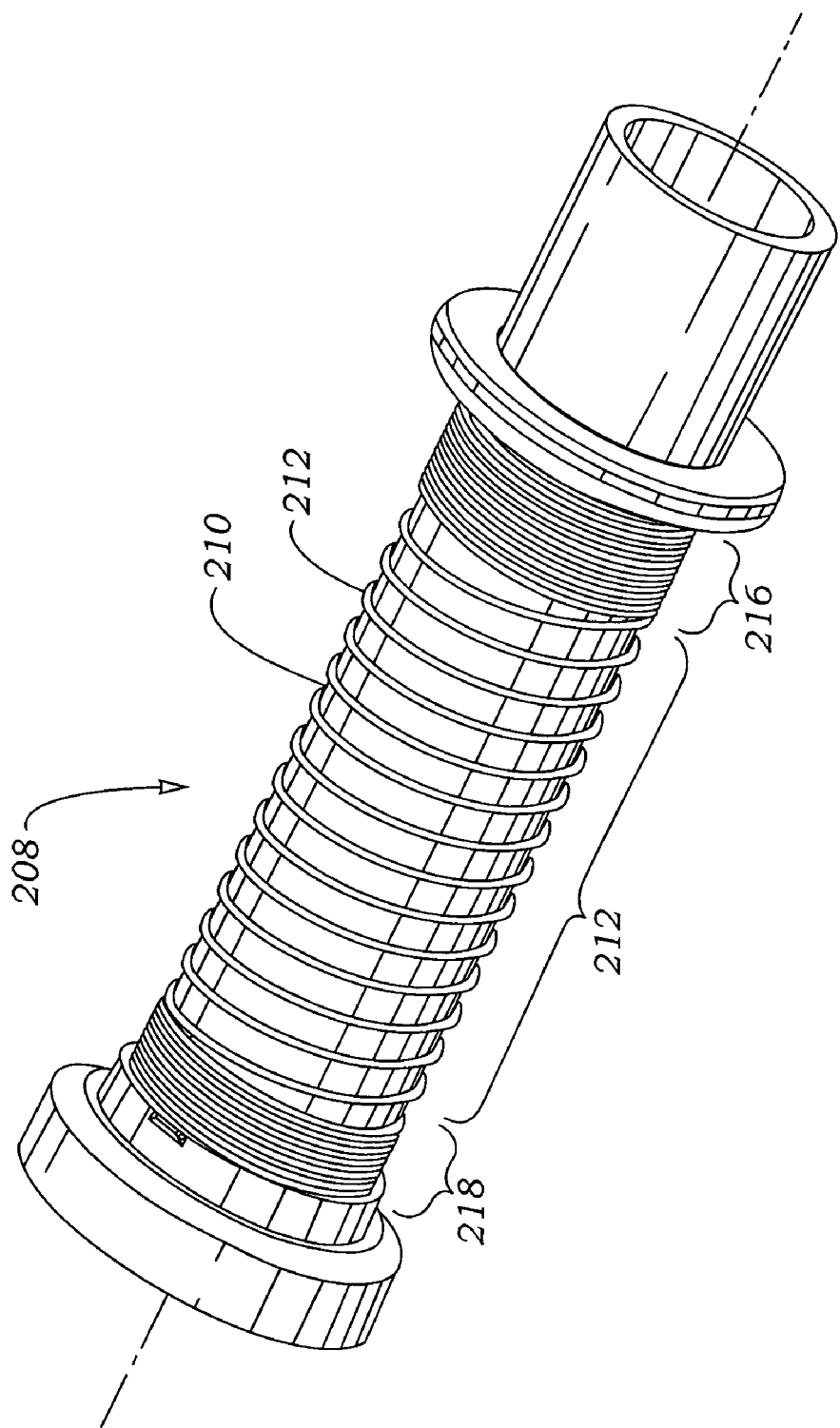

FIG. 3 illustrates another embodiment of the invention, comprising a non-delaminable kink-resistive conduit 208 having a first end 216, a second end 218, and a middle portion 214, for use as an inflow conduit of a ventricular assist device. In one embodiment, the tubular wall 210 comprises a substantially porous PTFE tubular substrate with a layer of FEP wrapped around it and substantially non-delaminably bonded thereto by a method of the invention. As will be described, the material and construction of conduit 208 is sufficiently flexible while at the same time being sufficiently able to withstand collapse. A plurality of external reinforcing members 212 comprises a series of coils of a continuous rib having a circular or semi-circular cross-section projecting outward from the FEP layer. The reinforcement coils 212 extend generally between first end 216 and second end 218 and are preferably axially spaced apart in middle portion 214 while being more tightly spaced (even in contact) at ends 216, and 218. The loosely spaced middle portion 214 permits conduit 208 to bend, and the tightly spaced regions 216, and 218, provide rigidity in the areas adjacent associated coupling structures. This helps the surgeon in connecting conduit in its proper place.

Another function of external reinforcing members 212 is to provide "burst strength" (also called "hoop strength") to the conduit. Burst strength and hoop strength refer to the ability of the conduit to withstand the force of internal pressure, which is a product of the action of the ventricle and the mechanical pump. The external reinforcing members provide a binding that acts to increase the burst strength.

The PTFE tubular substrate may be formed by various means well known in the art, such as, for example, extrusion followed by expansion. External reinforcement members 212 may be formed by various means well known in the art, such as, for example, extrusion. In a particularly preferred embodiment, reinforcement members 212 preferably comprise a monofilament helically wrapped around tubular wall 210 and non-delaminably bonded thereto.

The present invention is directed to a method of substantially non-delaminably bonding a substantially non-porous thermoplastic elastomer to a substrate that can be used for the production of valuable products, including non-thrombogenic products. The method comprises the steps of selecting a substantially non-porous thermoplastic elastomer having a melting point substantially below the melting point of the substrate, forming a bilayer comprising a layer of the selected thermoplastic elastomer in contact with a layer of the substrate, heating the bilayer to a predetermined temperature near the melting point of the thermoplastic elastomer but substantially below the melting point of the substrate, maintaining the bilayer at the predetermined temperature for a predetermined period of time, and, allowing the heated bilayer to cool to ambient temperature, whereby the thermoplastic elastomer is substantially non-delaminably bonded to the substrate.

The selected thermoplastic elastomer may be a biocompatible polymer. The substrate may be porous or non-porous— for example non-porous ePTFE. Nonthrombogenic products may be obtained using the method. Additional examples of substrates that can be used in connection with the method include ePTFE having an internodular distance up to about 300.mu., ePTFE having an internodular distance up to about 200.mu., ePTFE having an internodular distance up to about 100.mu., ePTFE having an internodular distance up to about 50.mu., and ePTFE having an internodular distance up to about 5.mu.

When the method is applied to substantially porous PTFE, the product obtained may be non-thrombogenic. The selected thermoplastic elastomer may be biocompatible polymer, for example FEP. The temperature and times employed in the process are a function of the melting points of the substrate and the thermoplastic elastomer. The inventor believes, but is not certain, that the success of the process in affording a non-delaminable bond rests on the ability of the thermoplastic elastomer to "wet" the surface of the substrate. The inventor believes, but is not certain, that this "wetting" is one of the factors that makes it possible to form short range van der Waals attractive forces to produce adhesion between the surfaces of the elastomer and the substrate. In addition, the inventor believes, but is not certain, that the thermoplastic sealant flows into any existing porosity in the substrate to create a non-delaminable bond. To make both of these phenomena possible, it is necessary for the elastomer to become sufficiently mobile to undertake the "wetting" and flowing processes. Thus, the elastomer must be heated to a predetermined temperature near its melting point, but substantially below the melting point of the substrate.

In the case involving porous PTFE as substrate and FEP as thermoplastic elastomer, the porous PTFE has a melting point substantially in the range of 325.degree. C. to 343.degree. C. By contrast, the FEP has a melting point substantially in the range of 240.degree. C. to 290.degree. C. Here, the predetermined temperature for the process is between at least about 260.degree. C. and about 300.degree. C. More preferably, the predetermined temperature for the process is between at least about 275.degree. C. and about 285.degree. C. Furthermore, in this case the predetermined time for heating at this temperature is between at least about 10 minutes and about 30 minutes. More preferably, in this case the predetermined time for heating at this temperature is between at least about 15 minutes and about 25 minutes.

The substantially non-porous thermoplastic elastomer substantially non-delaminably bonded to the flexible porous tubular substrate in accordance with the method of the invention can be used in a substantially non-porous conduit which comprises a flexible, porous tubular substrate having a first end, a second end, and a middle portion wherein the porous tubular substrate may be made of a biocompatible polymer such as PTFE. The PTFE may be closed structured to resist tissue ingrowth from the exterior of the tubular substrate. In various embodiments, the PTFE further may have a pore size of less than about 20.mu., less than about 15.mu., or less than about 2.mu. In this conduit, the water entry pressure for the tubular substrate may be at least about 5 psi (0.34 atm). In various embodiments of the conduit, the elastomer may be FEP, and the substrate may be made of at least one polymer selected from the group consisting of PTFE, FEP, PFA (perfluoroalkoxy), PPS, PVDF (polyvinylidene fluoride), PEEK, PS/PES, PCTFE, and ETFE. In further embodiments, the elastomer may be a extruded or skived non-porous tape made from PTFE, FEP, PFA (perfluoroalkoxy), PPS, PVDF (polyvinylidene fluoride), PEEK, PS/PES, PCTFE, and ETFE, vinylidene polymer plastics, polyethylene, polypropylene, polyesters, polyamides, polyethylene terephthalate, high density polyethylene, irradiated polyethylene, polycarbonates, polyurethanes, polyvinyl chloride, polyester copolymers and polyolefin copolymers.

The invention also teaches a method for providing a substantially non-delaminable external kink-resistive supporting structure for the conduit comprising the steps of selecting a thermoplastic polymer monofilament having a melting point up to about the melting point of the elastomer, helically winding the filament around the conduit to form a supported conduit, heating the supported conduit to a predetermined temperature up to about the melting point of the thermoplastic elastomer, maintaining the supported conduit at the predetermined temperature for a predetermined period of time, and, allowing the heated supported structure to cool to ambient temperature.

A kink-resistive conduit produced in accordance with the method is shown in FIG. 3. The polymer monofilament may be a polypropylene, PTFE, or FEP monofilament. In a further embodiment of the method, the filament is helically wound around the conduit, wherein the helical winding is wound more tightly at the first end and second ends than in the middle of the conduit, to form a supported conduit as shown in FIG. 3. In this embodiment, likewise, the polymer monofilament may be a polypropylene, PTFE, or FEP monofilament.

The substantially non-porous conduits of the invention may be used to form an inflow conduit for an implantable ventricular assist device comprising, in combination the substantially non-porous conduit, wherein the substantially non-porous conduit has a substantially smooth inner surface for enhanced flow-through of blood with a minimum of surface-induced turbulence, a ventricular attachment structure to which said first end of said substantially non-porous conduit connects, and a coupling fitting on the second end of the substantially non-porous conduit. Such a conduit may be used to form an implantable ventricular assist device in combination with an implantable pumping portion in flow communication with the inflow conduit, and an outflow conduit in flow communication with the pumping portion.

A method for the treatment of congestive heart failure comprises implanting the implantable ventricular assist device described in the foregoing paragraph in a patient in need of such treatment wherein said implantation is effective to ameliorate one or more of the symptoms of the heart failure. The implantable ventricular assist device may be packaged in the packaging material, wherein the device is effective for implantation in a patient afflicted with congestive heart failure, and the packaging material includes a label that indicates that the device is effective for such implantation.

Still another embodiment of a substantially non-delaminable kink-resistive conduit, is made by selecting a flexible, porous tubular substrate having a first end, a second end, and a middle portion; selecting a thermoplastic polymer monofilament having a melting point up to about the melting point of the tubular substrate; winding the filament around the middle portion of the substrate to form a supported substrate; heating the supported substrate to a first predetermined temperature up to about the melting point of the thermoplastic polymer; maintaining the supported substrate at the first predetermined temperature for a first predetermined period of time; allowing the heated supported substrate to cool to ambient temperature; selecting a substantially non-porous thermoplastic elastomer having a melting point substantially below the melting point of the substrate; wrapping a layer of the selected thermoplastic elastomer around the cooled supported substrate to form a wrapped supported substrate; heating the wrapped supported substrate to a second predetermined temperature near the melting point of the thermoplastic elastomer but substantially below the melting point of the substrate; maintaining the wrapped supported substrate at the second predetermined temperature for a second predetermined period of time; and, allowing the heated wrapped supported substrate to cool to ambient temperature; whereby the thermoplastic polymer, the thermoplastic elastomer, and the substrate are substantially non-delaminably bonded to form a substantially non-delaminable kink-resistive conduit.

A further embodiment comprises products and a method to make them, comprising forming a supported conduit that is substantially non-delaminable and substantially non-porous. The method involves the steps of selecting a flexible, porous taenoid substrate and a taenoid substantially non-porous thermoplastic elastomer having a melting point substantially below the melting point of the taenoid porous substrate. A taenoid bilayer comprising a layer of the taenoid thermoplastic elastomer in contact with a layer of the taenoid porous substrate is formed and heated to a first predetermined temperature near the melting point of the taenoid thermoplastic elastomer but substantially below the melting point of the taenoid porous substrate and maintaining the bilayer at that temperature for a first predetermined period of time. The bilayer is allowed to cool to ambient temperature to afford a non-delaminable taenoid bilayer which is helically wound around a tubular substrate in a manner whereby the taenoid thermoplastic elastomer layer is in contact with the tubular substrate to form a wound substrate. The purpose of the taenoid bilayer is to impart burst strength to the product of the method. The flexible tubular substrate may be a woven substrate, or an ePTFE having an internodular distance up to about 300.mu. It may be porous or not, but is desirably non-thrombogenic. The thermoplastic non-porous polymer used in the invention is advantageously FEP, but other such polymers may be suitable. The wound substrate is heated to a second predetermined temperature up to about the melting point of the taenoid thermoplastic polymer, and maintained for a second predetermined period of time. The heating may be carried out by keeping the tubular substrate on a mandrel heated by resistance wires, infrared heating, or the like heating means. Likewise, the mandrel may additionally be provided with cooling means, for example internal passages for refrigerant liquids, as a resource for any required cooling. The heated wound substrate is allowed to cool to ambient temperature, and a substantially non-porous thermoplastic elastomer having a melting point substantially below the melting point of the tubular substrate is wrapped around the cooled supported substrate to form a wrapped substrate. The latter is heated to a third predetermined temperature up to about the second predetermined temperature of the method and maintained there for a third predetermined period of time. The resulting wrapped substrate is allowed to cool to ambient temperature. A thermoplastic polymer monofilament is wound around the wrapped substrate to form a filamented substrate, which is heated to a fourth predetermined temperature up to about the second predetermined temperature and maintained there for a fourth predetermined period of time. After cooling, the tubular substrate, the taenoid bilayer, the thermoplastic polymer monofilament, and the thermoplastic elastomer are substantially non-delaminably bonded to form a substantially non-delaminable substantially non-porous supported conduit.

The first predetermined temperature, the second predetermined temperature, the third predetermined temperature, and the fourth predetermined temperature may be each between at least about 260.degree. C. and about 300.degree. C., more preferably between at least about 275.degree. C. and about 295.degree. C. The first predetermined time, the second predetermined time, the third predetermined time, and the fourth predetermined time may be each between at least about 10 minutes and about 30 minutes, and more preferably between at least about 15 minutes and about 25 minutes.

The flexible tubular substrate may be made of a biocompatible polymer such as PTFE, which may be closed structured to resist tissue ingrowth from the exterior of the flexible tubular substrate. Here, the PTFE may have a pore size of less than about 20.mu. In fact, the flexible tubular substrate may be made of made of at least one polymer selected from the group consisting of PTFE, FEP, PFA (perfluoroalkoxy), PPS, PVDF (polyvinylidene fluoride), PEEK, PS/PES, PCTFE, and ETFE. The water entry pressure for the flexible tubular substrate may be at least about 5 psi (0.34 atm).

The porous taenoid substrate, the taenoid thermoplastic elastomer, the tubular substrate, the selected thermoplastic elastomer, and the filament may each be a biocompatible polymer—for example, the thermoplastic elastomer may be FEP. The thermoplastic polymer monofilament may be a polypropylene, PTFE or FEP or the like monofilament.

82. An inflow conduit for an implantable ventricular assist device may be fabricated using a supported conduit having a substantially smooth inner surface for enhanced flow-through of blood with a minimum of surface-induced turbulence, attached at one end to a ventricular attachment structure and at the other to a coupling fitting. This may be used to construct an implantable ventricular assist device, further comprising an implantable pumping portion in flow communication with the inflow conduit; and, an outflow conduit in flow communication with the pumping portion. The completed implantable ventricular assist device may be used for the treatment of congestive heart failure, by implantation of the device in a patient in need of such treatment, wherein the implantation is effective to ameliorate one or more of the symptoms of the heart failure. This device may be packaged together with a label that indicates that the device is effective for such implantation.

Thus it will be appreciated that the invention provides a new and improved inflow conduit for an implantable ventricular assist device. It should be understood, however, that the foregoing description of the invention is intended merely to be illustrative thereof and that other modifications in embodiments may be apparent to those skilled in the art without departing from its spirit. For example, whereas the invention has been illustrated in connection with an LVAD, it may be used with other VAD's. Additionally, although the illustrative embodiment has been described in connection with an improved PTFE inflow conduit for an implantable ventricular assist device, a properly supported knitted fabric inflow conduit, such as described in my U.S. Pat. No. 6,001,056 could also be used.

On this basis, the instant invention should be recognized as constituting progress in science and the useful arts, and as solving the problems in cardiology and medicine enumerated above. In the foregoing description, certain terms have been used for brevity, clearness and understanding, but no unnecessary limitation is to be implied therefrom beyond the requirements of the prior art, because such words are used for descriptive purposes herein and are intended to be broadly construed.

Having described preferred embodiments of the invention with reference to the accompanying drawings, it is to be understood that the invention is not limited to those precise embodiments, and that the various changes and modifications may be effected therein by one skilled in the art without departing from the scope or spirit of the invention as defined in the appended claims. For example, the product can have other shapes, or could make use of other plastics. Thus, the scope of the invention should be determined by the appended claims and their legal equivalents, rather than by the examples given. All changes that come within the meaning and range of equivalency of the claims are to be embraced within their scope.

Definitions

Unless defined otherwise, all technical and scientific terms used herein have the same meaning as is commonly understood by one of skill in the art to which this invention belongs. All patents and publications referred to herein are incorporated in their entirety by reference.

All abbreviations for fluorocarbon polymers used herein have the same meaning as is commonly understood by one of skill in the art to which this invention belongs. As an example, PTFE refers to polytetrafluoroethylene. As a further example, FEP refers to poly(tetrafluoroethylene-co-hexafluoropropylene). As further examples, the following fluorocarbon polymers are commercially available from Fluorocarbon Company Limited, Caxton Hill, Hertford SG13 7NH, UK: PFA (perfluoroalkoxy), PPS, PVDF (polyvinylidene fluoride), PEEK, PS/PES, PCTFE, and ETFE.

All terms for polymers used herein have the same meaning as is commonly understood by one of skill in the art to which this invention belongs. As an example, the terms "resin", "polymer", and "elastomer" may be used synonymously by one of skill in the art to which this invention belongs.

All melting points and other physical constants for polymers and other substances as used herein have the same meaning and values as are commonly understood by one of skill in the art to which this invention belongs. For example, typical values for the melting points for the following fluorocarbon resins are: PTFE: 325.degree. C. to 343.degree. C.; FEP: 240.degree. C. to 290.degree. C.; PFA: 302.degree. C. to 310.degree. C.; ETFE: 254.degree. C. to 279.degree. C.; CTFE: 210.degree. C.; and: ECTFE: 240.degree. C.

As used herein, a bilaminate structure is a structure comprising two layers. As used herein, a non-delaminable structure is a structure comprising at least two layers wherein the layers cannot be pulled apart or separated from each other without destroying the structural integrity of the individual layers.

As used herein, the internodular distance in a sample of expanded PTFE is the mean distance between nodes in the material as seen under a microscope. The microscopic nodes in a sample of expanded PTFE are microscopic areas of condensed polymer. The nodes are separated from each other by microscopic strands of polymer.

As used herein, a supported conduit is any tube-like structure incorporating reinforcement elements that act against the bursting and/or collapse of said conduit.

As used herein, the term taenoid refers to a coiled, ribbon-like, tape-like, or band-like structure, such as a headband.

What is claimed is:

1. A substantially non-delaminable and non-porous conduit which comprises:
   a flexible, tubular substrate having a first end, a second end, and a middle portion, the tubular substrate further having a melting point;
   a substantially non-porous thermoplastic elastomer having a melting point substantially below the melting point of said tubular substrate;
   a thermoplastic polymer monofilament; and
   a substantially non-delaminable taenoid bilayer comprising:
      a flexible, porous taenoid substrate; and, a substantially non-porous taenoid thermoplastic elastomer substantially non-delaminably bonded to said taenoid substrate, wherein said taenoid thermoplastic elastomer has a melting point substantially below the melting point of the taenoid substrate;

wherein the taenoid thermoplastic elastomer is substantially non-delaminably bonded to the taenoid substrate by: forming a bilayer comprising a layer of said taenoid thermoplastic elastomer in contact with a layer of said taenoid substrate; heating said bilayer to a predetermined temperature near the melting point of said taenoid thermoplastic elastomer but substantially below the melting point of said taenoid substrate; maintaining said bilayer at said predetermined temperature for a predetermined period of time; and allowing said heated bilayer to cool to ambient temperature to afford the substantially non-delaminable taenoid bilayer;

wherein the substantially non-delaminable taenoid bilayer is secured to the flexible, tubular substrate to create a wound substrate by:

helically winding said non-delaminable taenoid bilayer around said tubular substrate in a manner whereby said taenoid thermoplastic elastomer layer is in contact with said tubular substrate to form the wound substrate;

heating said wound substrate to a second predetermined temperature up to about the melting point of said taenoid thermoplastic polymer;

maintaining said wound substrate at said second predetermined temperature for a second predetermined period of time;

allowing said heated wound substrate to cool to ambient temperature;

wherein the substantially non-porous thermoplastic elastomer is secured to the wound substrate to form a wrapped substrate by;

wrapping a layer of said substantially non-porous thermoplastic elastomer around said cooled wound substrate to form the wrapped substrate;

heating said wrapped substrate to a third predetermined temperature up to about said second predetermined temperature;

maintaining said wrapped substrate at said third predetermined temperature for a third predetermined period of time;

allowing said heated wrapped substrate to cool to ambient temperature;

wherein the thermoplastic polymer monofilament is secured to the wrapped substrate to form a filamented substrate by;

winding said filament around said wrapped substrate to form the filamented substrate;

heating said filamented substrate to a fourth predetermined temperature up to about said second predetermined temperature;

maintaining said filamented substrate at said fourth predetermined temperature for a fourth predetermined period of time; and, allowing said heated filamented substrate to cool to ambient temperature;

whereby said tubular substrate, said taenoid bilayer, said thermoplastic polymer monofilament, and said thermoplastic elastomer are substantially non-delaminably bonded to form the substantially non-delaminable substantially non-porous conduit.

2. The conduit according to claim 1, wherein said flexible, tubular substrate is made of a biocompatible polymer.

3. The conduit according to claim 2, wherein said biocompatible polymer is PTFE.

4. The conduit according to claim 3, wherein said PTFE is closed structured to resist tissue ingrowth from the exterior of said tubular substrate.

5. The conduit according to claim 3, wherein said PTFE has a pore size of less than about 20 microns.

6. The conduit according to claim 3, wherein said PTFE has a pore size of less than about 15 microns.

7. The conduit according to claim 3, wherein said PTFE has a pore size of less than about 2 microns.

8. The conduit according to claim 2, wherein said elastomer is FEP.

9. The conduit according to claim 1, wherein said flexible, tubular substrate is made of at least one polymer selected from the group consisting of PTFE, FEP, PFA (perfluoroalkoxy), PPS, PVDF (polyvinylidene fluoride), PEEK, PS/PES, PCTFE, and ETFE.

10. The conduit according to claim 1, wherein said substantially non-porous thermoplastic elastomer is non-porous PTFE tape.

11. The conduit according to claim 1, wherein said substantially non-porous thermoplastic elastomer is non-porous FEP tape.

12. The conduit according to claim 1, wherein said substantially non-porous thermoplastic elastomer is selected from the group consisting of non-porous tapes made from PFA (perfluoroalkoxy), PPS, PVDF (polyvinylidene fluoride), PEEK, PS/PES, PCTFE, and ETFE.

13. The conduit according to claim 1, wherein said substantially non-porous thermoplastic elastomer is selected from the group consisting of vinylidene polymer plastics, polyethylene, polypropylene, polyesters, polyamides, polyethylene terephthalate, high density polyethylene, irradiated polyethylene, polycarbonates, polyurethanes, polyvinyl chloride, polyester copolymers and polyolefin copolymers.

14. An inflow conduit for an implantable ventricular assist device comprising, in combination:

a substantially non-delaminable and non-porous conduit which comprises:
  a flexible, tubular substrate having a first end, a second end, and a middle portion, the tubular substrate further having a melting point;
  a substantially non-porous thermoplastic elastomer having a melting point substantially below the melting point of said tubular substrate;
  a thermoplastic polymer monofilament; and
  a substantially non-delaminable taenoid bilayer comprising:
    a flexible, porous taenoid substrate; and,
    a substantially non-porous taenoid thermoplastic elastomer substantially non-delaminably bonded to said taenoid substrate, wherein said taenoid thermoplastic elastomer has a melting point substantially below the melting point of the taenoid substrate;
  wherein the taenoid thermoplastic elastomer is substantially non-delaminably bonded to the taenoid substrate by: forming a bilayer comprising a layer of said taenoid thermoplastic elastomer in contact with a layer of said taenoid substrate; heating said bilayer to a predetermined temperature near the melting point of said taenoid thermoplastic elastomer but substantially below the melting point of said taenoid substrate; maintaining said bilayer at said predetermined temperature for a predetermined period of time; and allowing said heated bilayer to cool to ambient temperature to afford the substantially non-delaminable taenoid bilayer;

wherein the substantially non-delaminable taenoid bilayer is secured to the flexible, tubular substrate to create a wound substrate by:
helically winding said non-delaminable taenoid bilayer around said tubular substrate in a manner whereby said taenoid thermoplastic elastomer layer is in contact with said tubular substrate to form the wound substrate;
heating said wound substrate to a second predetermined temperature up to about the melting point of said taenoid thermoplastic polymer;
maintaining said wound substrate at said second predetermined temperature for a second predetermined period of time; and
allowing said heated wound substrate to cool to ambient temperature;

wherein the substantially non-porous thermoplastic elastomer is secured to the wound substrate to form a wrapped substrate by;
wrapping a layer of said substantially non-porous thermoplastic elastomer around said cooled wound substrate to form the wrapped substrate;
heating said wrapped substrate to a third predetermined temperature up to about said second predetermined temperature;
maintaining said wrapped substrate at said third predetermined temperature for a third predetermined period of time; and
allowing said heated wrapped substrate to cool to ambient temperature;

wherein the thermoplastic polymer monofilament is secured to the wrapped substrate to form a filamented substrate by;
winding said filament around said wrapped substrate to form the filamented substrate;
heating said filamented substrate to a fourth predetermined temperature up to about said second predetermined temperature;
maintaining said filamented substrate at said fourth predetermined temperature for a fourth predetermined period of time; and
allowing said heated filamented substrate to cool to ambient temperature;

whereby said tubular substrate, said taenoid bilayer, said thermoplastic polymer monofilament, and said thermoplastic elastomer are substantially non-delaminably bonded to form the substantially non-delaminable substantially non-porous conduit, said substantially non-delaminable and non-porous conduit having a substantially smooth inner surface for enhanced flow-through of blood with a minimum of surface-induced turbulence;

a ventricular attachment structure to which said first end of said substantially non-porous conduit connects; and, a coupling fitting on said second end of said substantially non-porous conduit.

15. The inflow conduit according to claim 14, wherein said flexible, tubular substrate is made of at least one polymer selected from the group consisting of PTFE, FEP, PFA (perfluoroalkoxy), PPS, PVDF (polyvinylidene fluoride), PEEK, PS/PES, PCTFE, and ETFE.

16. The inflow conduit according to claim 14, wherein said flexible, tubular substrate is made of PTFE.

17. The conduit according to claim 16, wherein said PTFE is closed structured to resist tissue ingrowth from the exterior of said tubular substrate.

18. The conduit according to claim 16, wherein said PTFE has a pore size of less than about 2 microns.

19. The conduit according to claim 14, wherein said substantially non-porous thermoplastic elastomer is non-porous PTFE tape.

20. The conduit according to claim 14, wherein said substantially non-porous thermoplastic elastomer is non-porous FEP tape.

* * * * *